United States Patent [19]

Carnahan et al.

[11] Patent Number: 5,420,424
[45] Date of Patent: May 30, 1995

[54] ION MOBILITY SPECTROMETER

[75] Inventors: Byron L. Carnahan, Pittsburgh; Alexander S. Tarassov, Mars, both of Pa.

[73] Assignee: Mine Safety Appliances Company, Pittsburgh, Pa.

[21] Appl. No.: 235,484

[22] Filed: Apr. 29, 1994

[51] Int. Cl.$^6$ .......................... H01J 49/40; H01J 49/42
[52] U.S. Cl. ...................................... 250/287; 250/292; 250/290; 250/281
[58] Field of Search ............... 250/287, 292, 290, 281, 250/282

[56] References Cited

U.S. PATENT DOCUMENTS

| | | | |
|---|---|---|---|
| 3,473,018 | 10/1969 | Brubaker | 250/292 |
| 4,831,254 | 5/1989 | Jenkins | 250/287 |
| 5,218,203 | 6/1993 | Eisele et al. | 250/287 |

FOREIGN PATENT DOCUMENTS

| | | | |
|---|---|---|---|
| 58-172854 | 10/1983 | Japan | 250/287 |
| 683516 | 12/1980 | U.S.S.R. | 250/287 |

Primary Examiner—Jack I. Berman
Attorney, Agent, or Firm—Titus & McConomy

[57] ABSTRACT

An ion mobility spectrometer having a housing with an analyzer positioned therein. The analyzer includes first and second longitudinally spaced apart electrodes which are preferably cylindrical in configuration. The space between the electrodes defines an analytical gap which is in communication with a source of carrier gas. An ionization source such as a β-emitter or corona discharge is juxtaposed with the analytical gap and source of sample media and includes an ion aperture for ions to enter said gap. The spectrometer includes an ion detector for measuring ions. An electrical controller connected to the first and second electrodes for impressing a first direct potential and second periodic asymmetrical potential capable of creating a transverse electrical field therebetween during the flow of carrier gas in the analytical gap. Preferably, a third low voltage ripple potential is impressed in series with the first two potentials. A third electrode, normally the ionization source, for electrically migrating the ions formed by the source into the analytical gap is positioned proximate to the ion aperture.

18 Claims, 6 Drawing Sheets

ION MOBILITY SPECTROMETER

FIELD OF THE INVENTION

The present invention relates to ion mobility spectrometry and in particular to an ion mobility spectrometer capable of both quantitative as well as qualitative analysis of trace level species.

BACKGROUND OF THE INVENTION

Ion Mobility Spectrometry ("IMS") is generally well known as a qualitative analytical tool. Basically, IMS separates ions by differences in the time it takes them to drift through a gas at atmospheric pressure in an applied electrostatic field. A sample gas alone or in combination with a carrier gas is directed into an ionization region containing a source of ionization, typically a $\beta$-emitter, and accelerated into a drift region where they are separated based on mass, charge and size of the ions. These ions are then registered by a detector such as an electrometer amplifier. An important variant of the IMS device is a transverse field compensation IMS which utilizes two electrodes to provide an analyzing region between the ionization zone and the ion detection region. The analyzing region is set to a selected set of potentials which permits certain ions to transverse the analytical region to reach a detector such as an electrometer.

Of particular interest is Russian Inventor's Certificate No. 966583 which uses a transverse field IMS to provide ion separation for qualitative analysis. Improved separation is achieved by impressing an alternating asymmetrical electric field in the analyzing region which is of fixed electrical polarity. As described therein, the ion velocity $V_d$, the ion mobility k and the electric field intensity E are related by: $V_d = k * E$. Ion mobility k can be expressed by the following equation: $k = k_o + k_2 E^2 + k_r E^4 + \ldots$ (1); where $k_i$'s are coefficients which depend upon the ion species under investigation. By impressing an asymmetric alternating electric field in the analyzing region, the mean drift velocity becomes:

$$V_d = k_o 1/T \int^t_{t+T} E(t)dt + k_2 1/T \int^t_{t+T} E^3(t)dt + \quad (2);$$

where T is the period of the electric field, t is the current time and $k_o$ is ion mobility when $E=0$. In an asymmetrical alternating electric field it can be seen from expression (2) that the mean drift velocity depends on the quadratic and higher order terms of the expansion for k given by Equation (1). The inventors disclosed that the maximum drift velocity can be reached if $E^+/E^- = 2$, where $E^+$, $E^-$ represent the amplitudes of the positive and negative polarities respectively.

In *International Journal of Mass Spectrometry and Ion Processes*, 128 (1993) pp 143–48, a method of ion separation in dense air-gas media is disclosed using high-frequency electric fields. The method disclosed is based upon the teachings of the Inventor's Certificate No. 966583, except for the use of a high-frequency (2 M Hz) asymmetrical electrical field and differently configured apparatus. The paper discloses a method for the detection of trace amounts of amines in gas air mixtures where the threshold detection of tertiary amines was from $3 \cdot 10^{-11}$ to $3 \cdot 10^{-10}$ g/liter. The time to record the spectrum under analysis was 10 seconds. The apparatus disclosed is stated to be capable of being made as a portable gas analyzer.

Other apparatus have been proposed. For example, U.S. Pat. No. 3,699,333 discloses a method and apparatus for sorting and detecting trace gases using ion-molecular reactions in a drift field located between an ion forming region and detection region. In U.S. Pat. No. 3,935,452 a quadrapole mobility spectrometer is described. This device utilizes a carrier gas mixed with gas and ions directed between the quadrapole electrode which has impressed therebetween a hyperbolic electric field.

More recently, improvements have been reported in the lower limits of detectibility for ion mobility instruments. In U.S. Pat. No. 5,218,203 a device is disclosed for restricting a sample gas from entering the drift region and limiting sample gas ions to such regions. This device preferably operates above atmospheric pressure.

Accordingly, it is an object of the present invention to provide a gas analyzer which can provide an extended dynamic range over a wide variety of ionic species. It is a further object of the invention to provide an IMS analyzer which provides a secondary and tertiary means of resolution. It is also an object of the invention to provide an ion spectrometer which can be made to be portable and detect trace levels of species in air at a threshold sensitivity of about $10^{-11}$ g/liter. It is also an object of the invention to provide an analysis of the species at a distance remote from the actual source of up to 10 cm or more. It is a further object of the invention to provide an analyzer for the remote detection of drugs or explosives or other chemicals for which detection is desired at very low threshold limits.

SUMMARY OF THE INVENTION

Generally, the present invention provides an ion mobility spectrometer which can be configured in a portable mode for the detection of species in the range of about $10^{-11}$ g/liter. In a preferred embodiment, the invention comprises a housing having a first sample media inlet and a media outlet. A second inlet or source of carrier gas is also provided into the housing. In most cases the sample media is a gas or vapor, however, solids such as proteins, virus, organic polymers, and the like can be sampled. The first inlet and outlet allow access of a gas to be sampled into the spectrometer, preferably by a small pump attached to the outlet. This configuration is particularly useful where the spectrometer is configured for use as a small portable detector used in detecting explosives or drugs.

Positioned within the housing is an analyzer which is made up of first and second spaced apart electrodes. The electrodes are preferably longitudinal to a gas flow and define an analytical gap. The analytical gap is defined by parallel or concentrically positioned electrodes depending upon whether the spectrometer is planar or cylindrical. The analytical gap is in direct communication with a second inlet or an internal source of carrier gas from a recirculation loop. An ion outlet is located at the end of the analytical gap opposite from the second inlet.

An ionization source is located in juxtaposition with the sample media inlet and the analytical gap. An ion aperture defines an opening to provide communication between the ionization source and the analytical gap so that ions created by the ionization source can migrate into the analytical gap preferably under the influence of an electric field. In the preferred embodiment, a small amount of carrier gas is encouraged through the aperture and away from the analytical gap to prevent non-ionized sample media from entering the gap. The ionizer may be a $\beta$-emitter, photoionizer, corona discharge ionizer, electrospray or thermal ionizer. An ionkicker (or device for supplying an electric field to assist in ion migration from the ionization source into the analytical gap) is positioned adjacent the aperture. The ionkicker can be a third electrode or part of the ionization structure itself.

In the present invention an electrical controller is connected to the first and second electrodes to impress first and second electrical potentials therebetween. A third electrode, normally the ionization source, is positioned proximate the ion aperture and connected to the electrical controller. The first electrical potential difference is a constant or slowly varying unidirectional compensating potential (hereinafter "compensation voltage") created between the first and second electrodes. The polarity of this potential difference depends upon the species to be detected. The second potential, in series with the first, is an asymmetrical periodic potential impressed between the first and second electrodes. The first and second electrical potentials cause the transverse oscillation of the ions in the analytical gap. Ions traversing the length of the gap exit through the ion outlet for detection and measurement.

An ion detector is located adjacent to the ion outlet and preferably includes a collector plate positioned adjacent to the outlet. Ions exiting the analytical gap are detected and measured on the collector plate. If specific species are sought to be detected, the biased collector plate can be connected to an electrometer amplifier to produce a signal upon detection of the desired species. On the other hand, if the invention is to be used to detect the presence of species, a record of ion current versus compensation voltage (hereinafter "ionogram") can be generated from the output of the collector when connected to a recording device. The spectrometer of the preferred embodiments can be packaged in a very small and light weight housing to facilitate portability or ease of handling. More importantly, control of the compensation and asymmetrical periodic potentials affords supervisory control over resolution while biasing of the ionkicker can be used to enhance the device's dynamic range. Other advantages of the invention will become apparent from a perusal of the following detailed description of presently preferred embodiments taken in connection with the accompanying drawings.

PRESENTLY PREFERRED EMBODIMENTS

Figure 1:
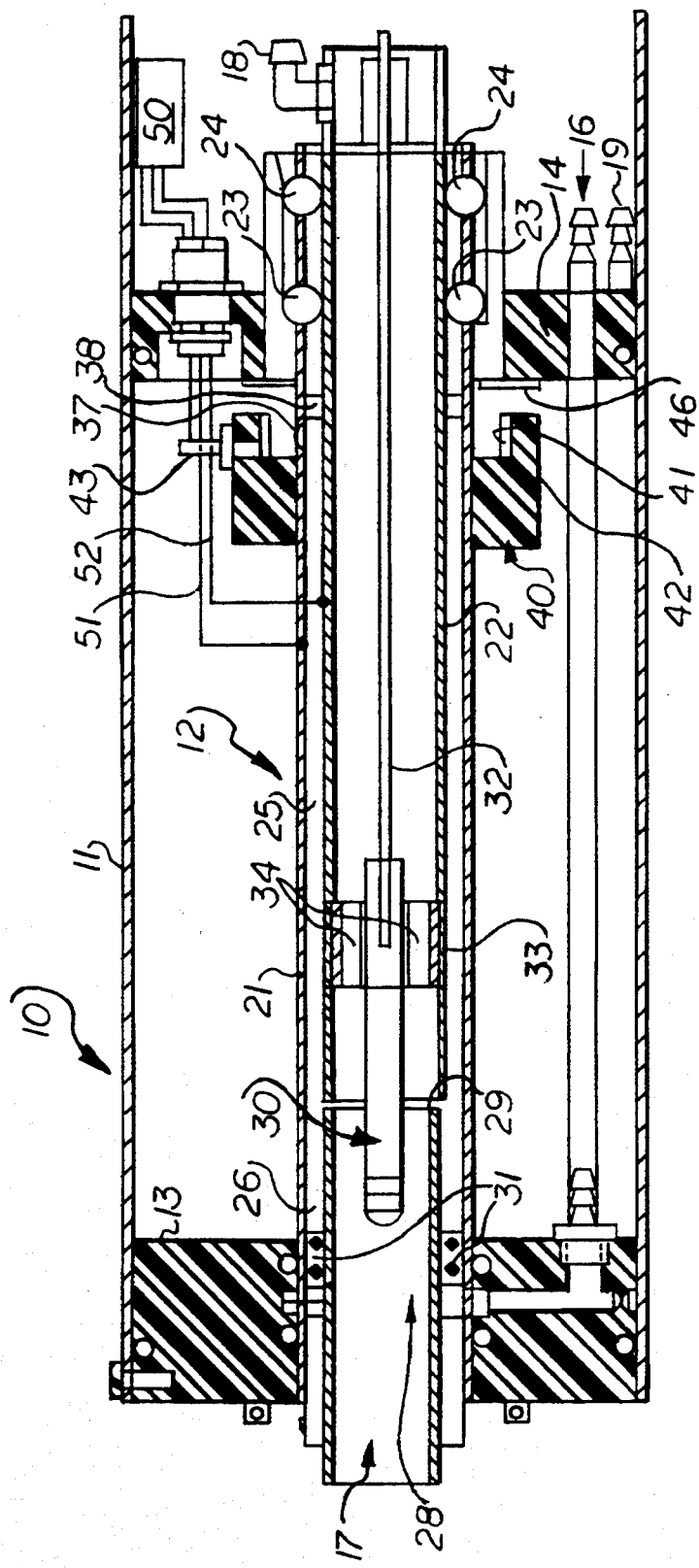
FIG. 1 is a schematic diagram of the ion spectrometer of the present invention.

Referring to FIG. 1, transverse ion mobility spectrometer 10 of the present invention comprises a housing 11 preferably made from a light weight material such as aluminum, brass or Lexan ® with a metal coating for shielding or to accept a common potential. In the preferred embodiment, housing 11 is cylindrical and approximately 65 mm in diameter and 250 mm in length. Positioned within housing 11 is analyzer 12 which is concentrically supported therein by means of support members 13 and 14, respectively. In one embodiment of the invention, analyzer 12 is planar and in a more preferred embodiment it is cylindrical. Support members 13 and 14 are made an insulating material such as Teflon ®, a ceramic or like rigid material.

Housing 11 includes first and second inlets 16 and 17 and outlets 18 and 19, respectively. First inlet 16 and outlet 19 are associated with a source of carrier gas such as dry air for carrying and/or diluting the species to be analyzed. In most instances, the carrier gas is located externally to housing 11, but in certain applications, such as where the spectrometer is portable, a closed loop between inlet 16 and outlet 19 can be configured with a filtering media interposed. In the latter case, only one inlet and outlet to the housing are required. Inlet 17 is connected to a source of media to be sampled. Such source can include a probe flexibly mounted to housing 11 and inlet 17 to obtain samples for detection and analysis. Preferably, at least one pump is connected to outlet 18 to draw the sampled gas through inlet 17 and analyzer 12. While not shown, the pump may be a vortex, diaphragm, vacuum or like pump capable of providing a slight negative pressure within analyzer 12. In a portable mode, the pump is powered by small rechargeable batteries, not shown.

Analyzer 12 comprises a first electrode 21 extending between and supported by support members 13 and 14, respectively. A second electrode 22 is precisely aligned concentrically within first electrode 21 by means of supports 23 and 24. In the planar configuration, electrodes 21 and 22 are elongated flat plates spaced in a parallel relationship, one to the other. In a cylindrical analyzer, electrodes 21 and 22 are cylinders in which electrode 22 is concentrically located within electrode 21. In such arrangement, supports 23 and 24 each comprise a plurality, e.g. two sets of three insulating balls made preferably of sapphire and positioned in a Teflon ® member, not shown. The space between first and second electrodes 21 and 22 defines analytical gap 25. The space defining analytical gap 25 is 1 to 3 mm and preferably about 2 mm having a length of from 8 to 12 mm. As shown in FIG. 1, where electrodes 21 and 22 are cylindrical, a preferred inner diameter of electrode 21 is 18 mm and the preferred outer diameter of electrode 22 is 14 mm.

Aligned and spaced apart from analytical gap 25 is an ionization source. In a preferred embodiment, the ionization source includes ionization chamber 28. Ionization chamber 28 is designed to separate the flow of carrier gas from the flow of sample media. In an arrangement shown in FIG. 1, chamber 28 defines a passageway 26 with electrode 21 for conveyance of a carrier gas. Passageway 26 includes a diffuser 31, in this embodiment, chamber 28 is preferably of a diameter slightly (e.g. 0.01 to 0.02 mm) less than the second electrode. The space between chamber 28 and analytical gap 25 is an ion aperture 29 which permits ionized species of the sample media to migrate into analytical gap 25. Aperture 29 is approximately 0.5 to 4 mm wide. Sample media from inlet 17 is directed into chamber 28 and ionized by ionizer 30. Ionizer 30 may consist of a $\beta$-source ionizer such as tritium for the production of negative and positive ions or may consist of an electronic ionizer such as a corona discharge, electrospray or a photoionization source. While $\beta$-ionization sources require regulatory agency licensing, they avoid additional electrical power requirements which is important for portable instruments. If electrical power is not a concern, it is preferable to utilize electronic or photoionization when portability is desired. As shown in FIG. 1, ionizer 30 is connected to electrode 32 which is supported adjacent, but spaced apart from second electrode 22 by spacer 33 made of insulating material and having a plurality of openings 34 therethrough to permit the passage of sample media. In this embodiment, ionizer 30 functions as a third electrode and part of the ionkicker.

At the end of electrode 21, adjacent to second support member 14, is at least one opening 37, and preferably a plurality of openings, e.g. eight, from analytical gap 25. Positioned adjacent to said openings 37 is plug 38 preferably made of an insulating material such as Teflon ® ceramic or like rigid material In a cylindrical configuration, plug 38 is annular and prevents the media in analytical gap 25 from exiting therefrom except though openings 37. Juxtaposed to openings 37 is ion detector 40.

Ion detector 40 comprises an collector plate 41 positioned normally or angularly offset (90°-45°) to the axes of openings 37. Collector plate 41 is preferably cantilevered over the openings by means of annular detector ring 42 made of an insulating material and having at least one lead 43 therethrough connected to collector plate 41. Preferably positioned on second support member 14 adjacent to openings 37 is disk electrode 46 used to help accelerate the ions toward collector place 41 by electrical migration. Ion species exiting openings 37 are detected on collector plate 41. Collector plate 41 is electrically connected to display or recording means for providing a signal upon detection of a threshold level of preselected species or for preparing ionograms to determine the constituents of a particular sampled media. Detector 40 is also preferably biased with a potential to accelerate the flow of ions to it.

An electrical controller 50 is provided to generate and control an electric potential between the first and second electrodes. A first compensating unidirectional voltage is supplied by controller 50 via line 51 to first electrode 21, which is generally operated at circuit common, and to second electrode 22 by line 52. Typically, the voltage supplied is in the range of ±10 to ±600 volts. Additionally, an asymmetrical periodic potential is impressed (in series with the unidirectional compensating potential) on second electrode 22 from controller 50 through line 52. Controller 50 can include portable rechargeable power sources such as NiCd or Li anode batteries known in the art. Generation of the asymmetric waveform can be accomplished through the use of conventional circuits including invertors and the like. Potentiometer, manual, or automatic sweeping or scanning can be used to vary the electric potential applied to the electrodes. Controller 50 is designed to provide the electrical condition necessary to resolve or map a specific ionic species.

Figure 2:
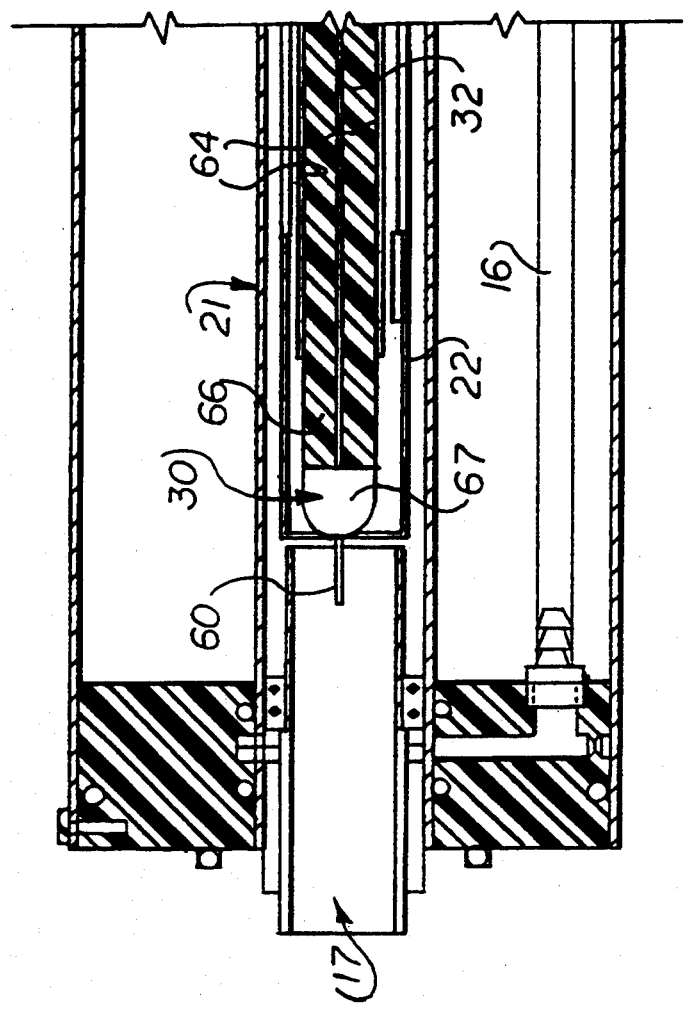
FIG. 2 is another embodiment of the invention shown in FIG. 1 using a corona discharge for ionization.

Referring to FIG. 2, a preferred embodiment of the invention is shown using a corona discharge for ionization. In this embodiment, ionization of the sample media is effected by corona discharge and takes place adjacent the tip of corona wire 60 of ionizer 30 which is connected to power controller 50 through electrode 32. The corona discharge wire 60 is driven by a bidirectional waveform, preferably an asymmetrical high voltage RF waveform. To prevent this RF from interfering with the analysis, namely, influencing electrode 22, electrode shield 64 is included. Electrode shield 64 is supported by insulator 66. Attached to the front of insulator 66 is the leading edge 67 of which is preferably rounded aluminum or like metal to reduce or eliminate turbulence of the sample media. Edge 67 is maintained at the same potential as electrode 32. Further, when using an asymmetrical waveform to drive the discharge, it is important to have the polarity of this waveform agree with that of the waveform which produces the asymmetrical potential impressed between first and second electrode 21 and 22, respectively.

In a preferred mode of operation of corona ionization, an asymmetrical high voltage RF waveform is used. Peak voltages of 2 kv have been found advantageous. Shield electrode 64 and electrode 32 as well as corona discharge wire 60 are set at the same d.c. voltage from about +20 vdc-~ +300 vdc for positive ions and from about −20 vdc to +600 vdc for negative ions. This has the effect of forcing the ions of ionization chamber 28 through ion aperture 29 into analytical gap 25.

OPERATION OF INVENTION

In a first preferred mode of operation, sample media is drawn into spectrometer 10 through inlet 17. Sample media may be, for example, ambient air being sampled to detect the presence of certain gases such as chlorine, toluene, benzene, the presence of an explosive such TNT, and like other ionizable materials. The sample media is drawn into ionization chamber 28 by the effect of a small pump creating a negative pressure at outlet 18. Coincidentally with sample media being drawn in to ionization chamber 28, carrier gas is introduced into plenum 26 through first inlet 16. The carrier gas acts as bulk transport mechanism for the ions moving longitudinally in gap 25. The carrier gas is preferably introduced so as to maintain a laminar flow through analytical gap 25. Plenum 26 is an annular chamber surrounding ionization chamber 28 in direct communication with analytical gap 25. Preferably, the carrier gas is dehumidified air. Presently, carrier gas is introduced at the inlet 17 in amount of from 2.5 to 5.0/min and is exhausted at the rate of 0.5 to 3.5 l/min. from outlet 19. The remaining flow is preferably directed through ion aperture 29 to be exhausted with sample media through outlet 18. This flow rate provides an analytical time of about 0.1 to 1.3 seconds in gap 25 depending upon the length of the gap. However, if the time is too long, none of the ions of interest get measured due to loss mechanisms such as diffusion and charge transfer.

Sample media drawn into chamber 28 is ionized by ionization source 30. If that source is tritium, positive and negative ions are created the same as with ionization by corona discharge. Presently, the radioactive source material is mounted on ionizer 30 which is connected to power controller 50 via electrode 32. Electrical potentials are applied to chamber 28, ionizer 30 (via electrode 32) and electrode 22, such that the ions formed in chamber 28 are driven through aperture 29 and into analytical gap 25. For positive ions the potentials applied to these electrodes would be: chamber 28; circuit common ionizer 30 and electrode 32, +20 to +300 vdc; electrode 22, compensation voltage typically between −1 and −100 vdc. For negative ions, the potentials applied to these electrodes would be: chamber 28; circuit common; ionizer 30 and electrode 32, −20 to −600 vdc; electrode 22, compensation voltage typically between +1 and +100 vdc. These same voltage configurations apply for operation of the corona discharge ionization, except shield electrode 64 is introduced between electrodes 22 and 32. In this case ionizer 30, electrode 32 and shield electrode 64 are maintained at the same dc potential while an additional high voltage RF potential is applied to ionizer 30 and electrode 32 which induces the corona breakdown at the tip corona discharge wire 60.

Once in the analytical gap 25, the ions move in the direction perpendicular to the direction of the air flow due to the influence of the asymmetric periodic potential impressed on the second electrode 22 by controller 50. The amplitude of the asymmetric periodic potential is in the range of 1 to 6 Kv and preferably in the range of about 2 to 5 Kv and more preferably about 3 Kv depending on the ionic species of interest. After the magnitude of the asymmetric voltage has been set, the compensation voltage can be held constant or scanned to provide separation of the ionic species.

The asymmetry $\beta$ of the periodic asymmetrical voltage of the present invention has a value of between about 0.1 to 0.7 (where 1=symmetry) for the waveform of the presently preferred embodiment. The waveform is identified by the expression $v = V_o [(1-\beta) \cos\omega t + \beta \cos 2\omega t]$. However, other waveforms may be used so long as they comply with the general expression $\int_o^T V^3(t) dt \neq 0$.

Due to the asymmetry of the second voltage and the nonlinearity of the ionic mobility at high electric field, ions move transversely in the analytical gap 25 at different rates. Uncompensated, the asymmetric field causes ions to strike the wall (electrodes) of gap 25. Those for which the mobility is appropriately compensated by the unidirectional compensating voltage will reach openings 37 and exit to register on detector 40. Detector 40 may include electrometric registration of ions such as taught and described in U.S. Pat. No. 3,668,388 which is incorporated by reference herein.

It has been found that a third bias voltage consisting of a low frequency (~100 Hz) "ripple" voltage impressed in series with the above mentioned voltages between electrodes 21 and 22 enhances the resolution in a cylindrical analyzer 12. This potential tends to narrow the effective gap between electrodes 21 and 22 and reduces the depth of the virtual potential well existing in gap 25 for those ions which are appropriately compensated.

Figure 8:
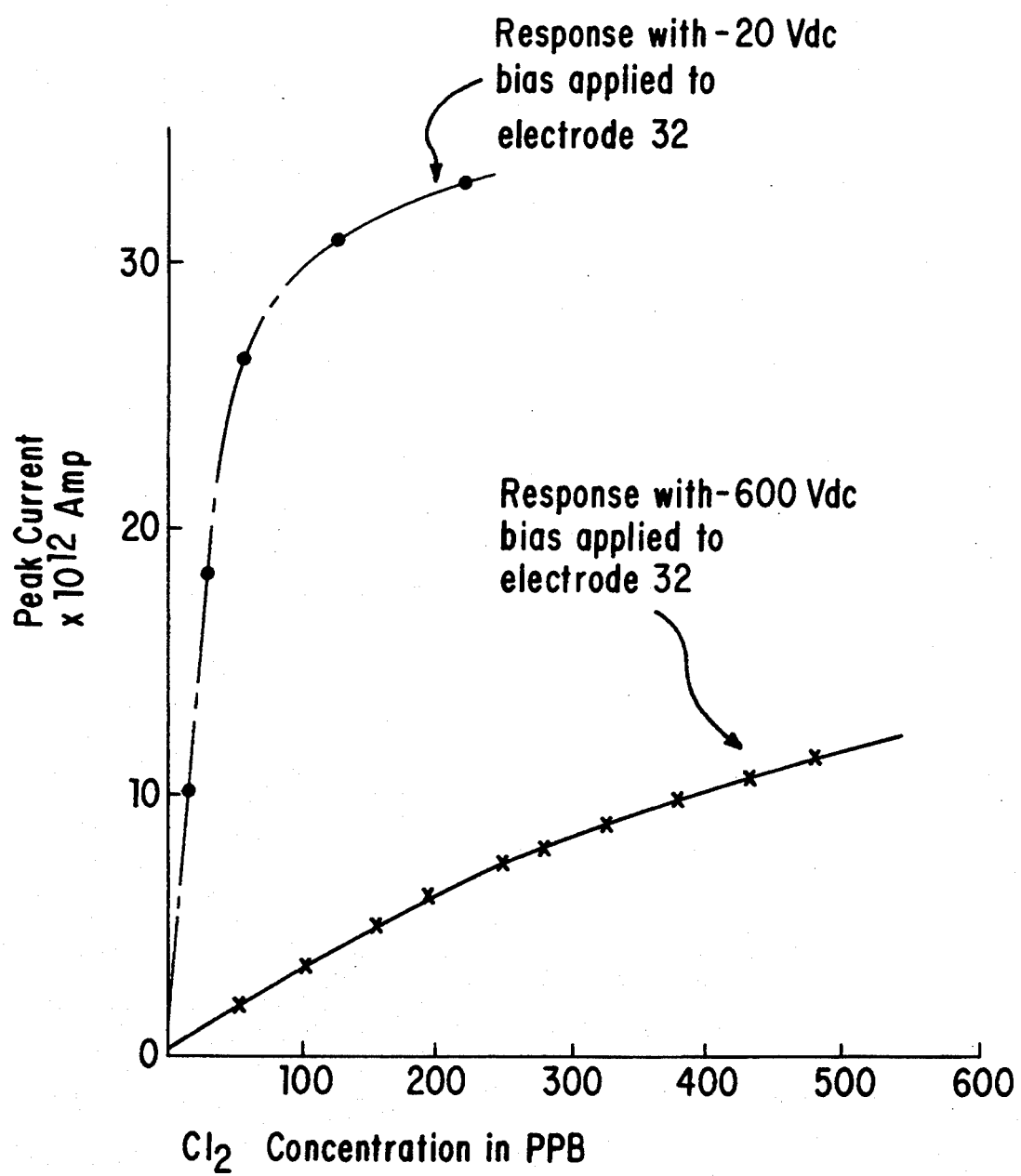
FIG. 8 is a graph showing the response of the present invention to chlorine in part per billion in air.

By changing the bias voltage applied to ionizer 30, the instrument's sensitivity and dynamic range can be adjusted. For example, as shown in FIG. 8 when the bias between chamber 28 and ionizer 30 is between −20 and −30 vdc, the sensor's response to $Cl_2$ is maximized. However, by increasing this voltage to −600 vdc, the sensitivity is reduced and the dynamic range is increased. This adjustment has no adverse affect on the sensor's resolution.

In accordance with equation (1), the amplitude of the second compensation voltage which must be applied between electrodes 21 and 22 will depend on the ion species of interest and the amplitude of the first asymmetric periodic voltage applied between electrodes 21 and 22. For a given ionic species, as the amplitude of the asymmetric voltage increases, the amplitude of the compensation voltage required for that species will likewise increase. The functional relationship between the amplitude of the periodic asymmetric voltage and the amplitude of the constant voltage required to compensate will depend on the identity of the ionic species involved. When the sample which enters via 17 contains several species of interest, the instrument's effective resolution can be increased by varying the amplitude of the periodic asymmetric voltage and monitoring the change in the shape of the ion spectra/ionogram.

Figure 5:
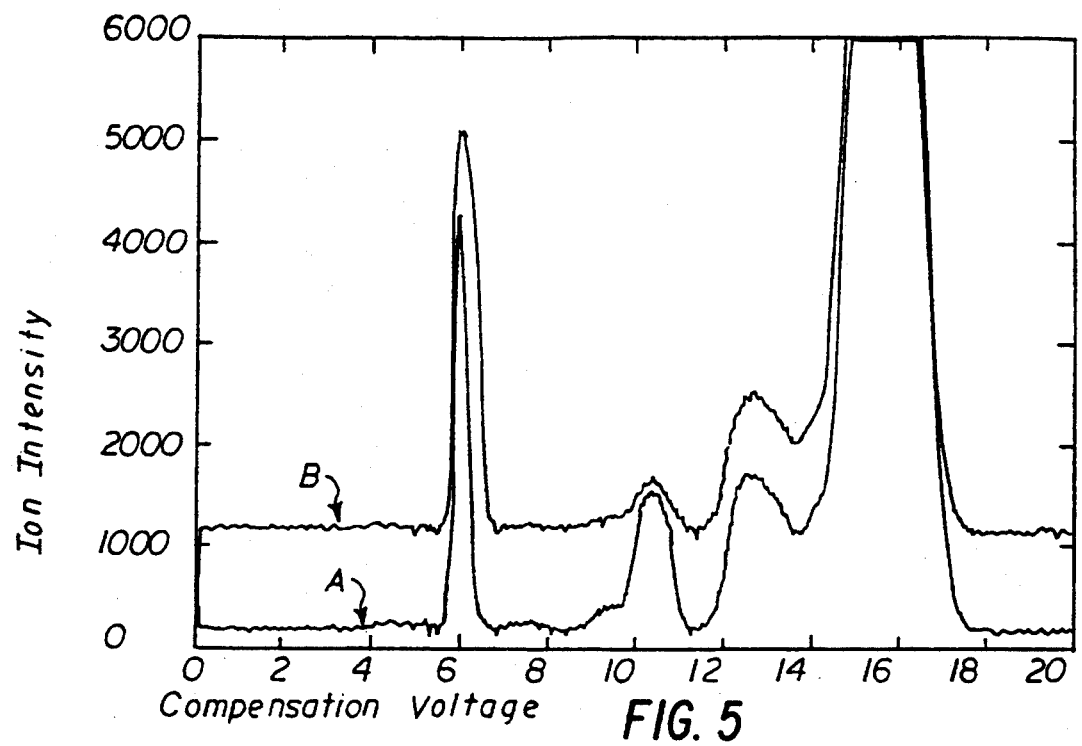
FIG. 5 are ionograms where the sample gas stream contained 100 ppm o-xylene in air, Curve A; and where the sample gas stream contained 100 ppm o-xylene and 10 ppb DMMP in air, Curve B.
Figure 6:
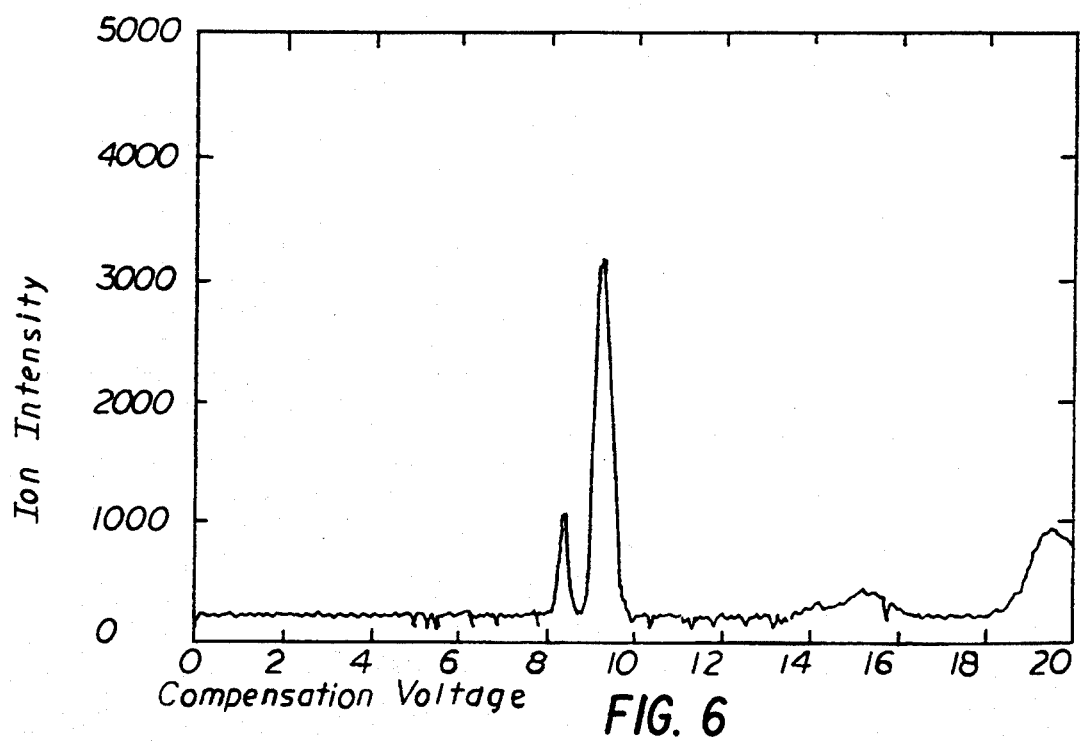
FIG. 6 is an ionogram where the sample gas stream contained 100 ppm o-xylene and 10 ppb DMMP in air and where the amplitude of the asymmetric period potential has been increased relative to the value it had in Curve B of FIG. 5.

An example of this procedure is shown below in FIG. 5 and 6. Curve A of FIG. 5 is an ionogram where the sample stream contained 100 ppm of o-xylene. Curve B of FIG. 5 is an ionogram recorded under conditions identical to those which existed with respect to Curve A, except the sample stream contained a combination of 100 ppm o-xylene and 10 ppb DMMP. In Curve A the o-xylene produces a strong feature in the ionogram at a compensation voltage of 6 V. As shown in Curve B, the feature due to DMMP occurs at almost the same compensation voltage. In FIG. 5, Curve B, it is difficult to isolate the o-xylene and DMMP related features, which impedes both qualitative and quantitative analysis of the original stream's composition. In FIG. 6, the amplitude of the periodic asymmetric voltage has been increased and transmission of both the o-xylene and DMMP related ion requires a higher compensation voltage. However the change in the compensation voltage for the o-xylene feature (6 to 8.2 V) is much less than the corresponding change for the DMMP feature (from 6.1 to 9.5 V), thus separating these two species and enabling the analysis of the original stream's composition.

The ionograms presented in FIGS. 3–6 show the response of spectrometer 10 to various gases which illustrates the advantage of the present invention. In these figures, various concentrations of dimethyl methyl phosphonate (DMMP) were used together with the organic compounds of benzene and xylene. Based upon these results, the lower detection limit for DMMP was determined to be below 0.1 ppb.

Figure 3:
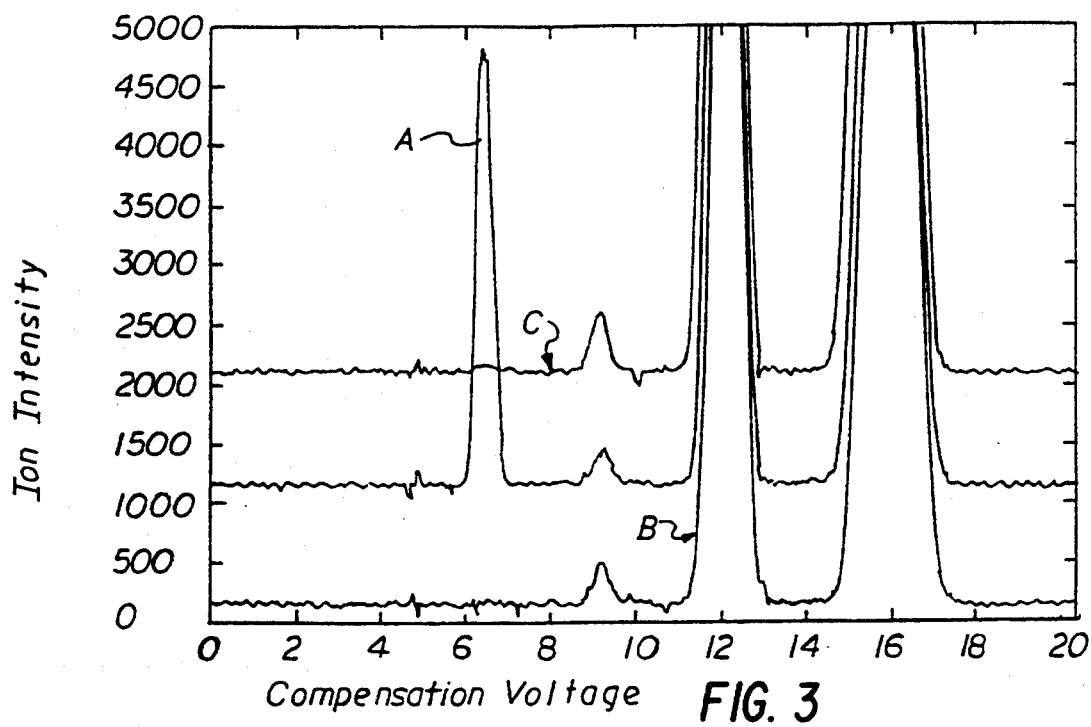
FIG. 3 is an ionogram where the sample gas stream contained 10 ppb of dimethyl methyl phosphonate (DMMP) in air.
Figure 4:
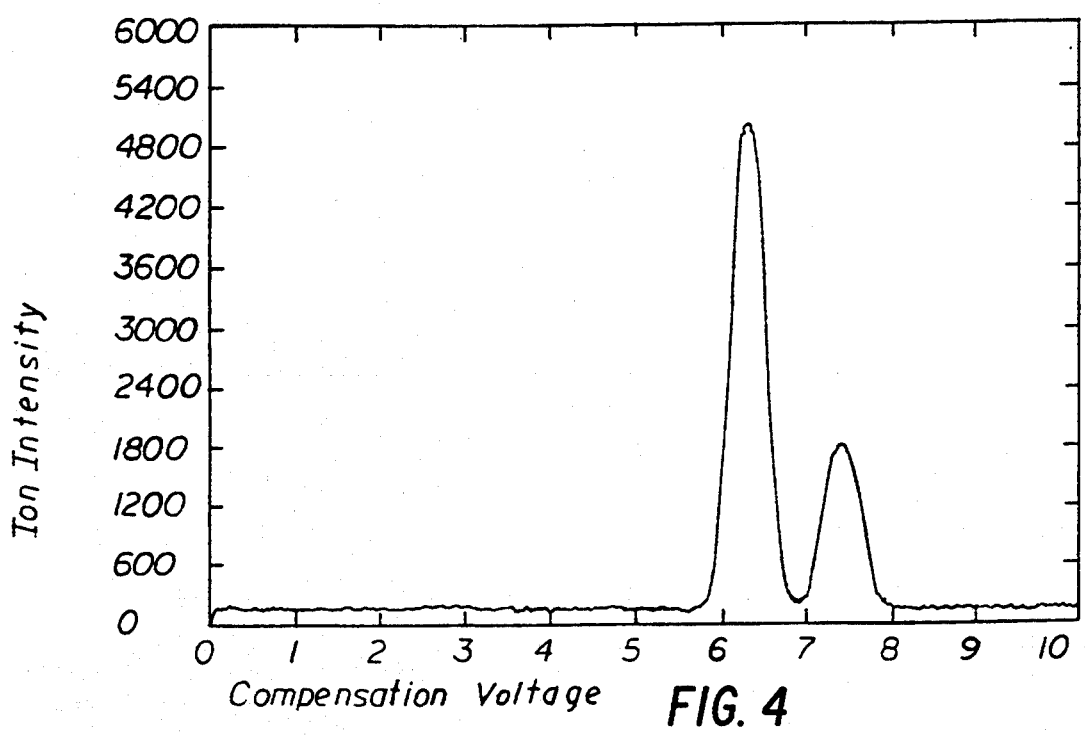
FIG. 4 is an ionogram where the sample gas stream contained 5 ppm benzene and 10 ppb dimethyl methyl phosphonate (DMMP) in air.

In FIG. 3, the middle curve A is the spectrum of ~10 ppb DMMP in clean air. Spectrum B and C, respectively, represent the clean air ionogram before and after spectrometer 10 was tested with DMMP. In FIG. 4, the ionogram represents a sample stream having 10 ppb DMMP and 5 ppm benzene. The DMMP peak at ~6 vdc and benzene at ~7.5 vdc are clearly shown. Similar tests with toluene produced ionograms likewise resolved.

Figure 7A:
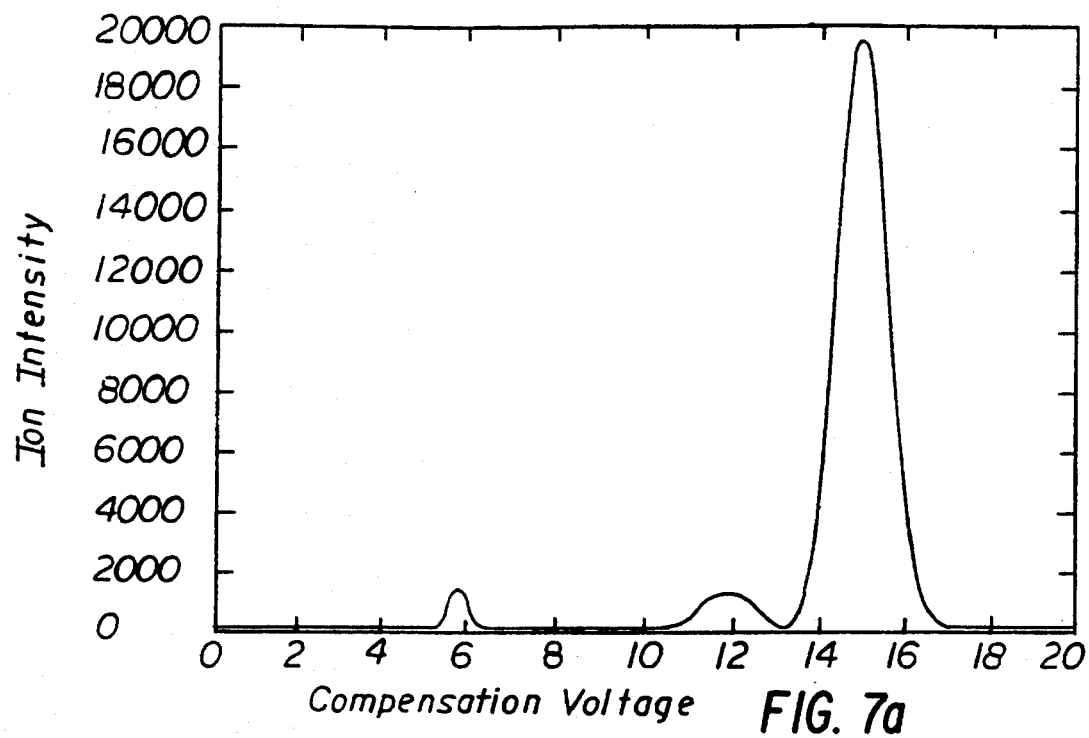
FIG. 7a is an ionogram where the sample gas stream contained 10 ppb DMMP in air and was ionized by beta radiation.
Figure 7B:
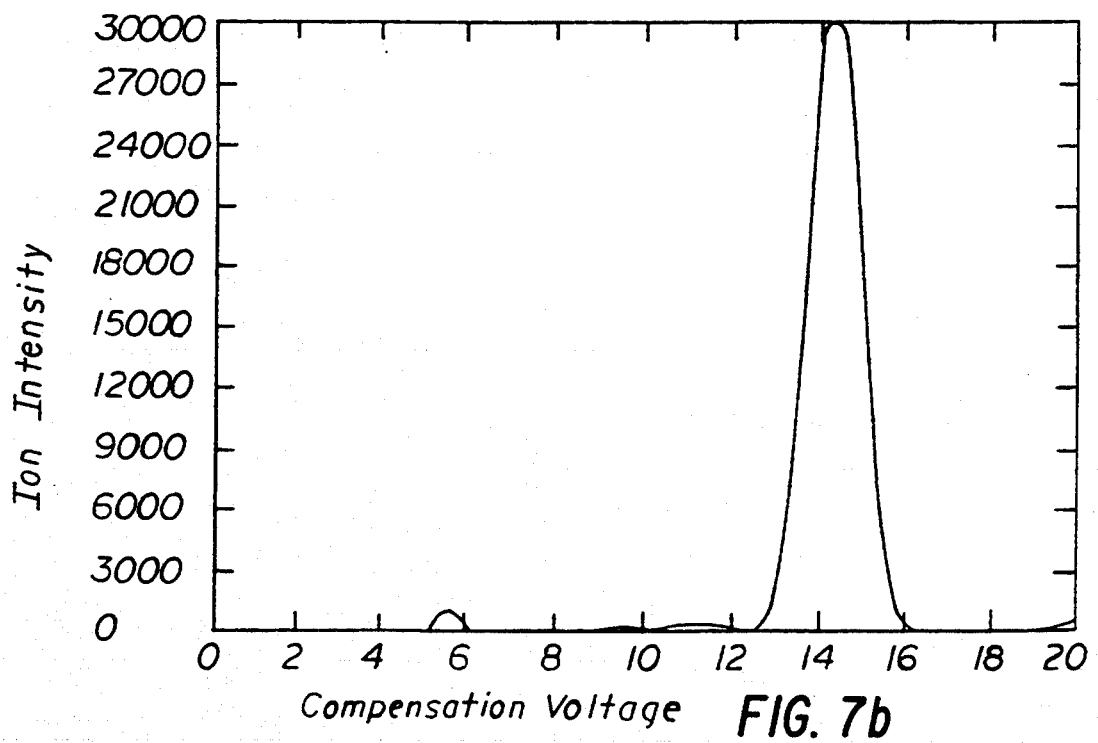
FIG. 7b is an ionogram where the sample gas stream contained 10 ppb DMMP in air and was ionized by corona discharge.

Referring to FIG. 7, two ionograms of DMMP in air are shown. For FIG. 7a, the sample media was ionized by traditional tritium $\beta$-emitter, while in FIG. 7b the ionization was produced by the corona discharge ionizer shown in FIG. 2. In FIG. 7b, an asymmetrical high voltage, having a peak amplitude of about 2 kv, was applied to discharge wire 60 via electrode 32 to form the corona discharge. The shield electrode 64 and electrode 32 were maintained at the same d.c. voltage $\sim +20$ volts.

While presently preferred embodiments of the invention have been shown and described, the invention may be otherwise embodied within the scope of the appended claims.

What is claimed is:

1. An ion mobility spectrometer comprising:
   a. a housing having at least one inlet for communication with a sample media and at least one outlet,
   b. an analyzer positioned within said housing comprising:
      i. at least first and second longitudinally spaced apart electrodes, said space between said electrodes defining a longitudinal analytical gap, said gap being in communication with a source of carrier gas for flow therethrough,
      ii. an ionization source juxtaposed with said analytical gap and in communication with said inlet for ionization of sample media,
      iii. an ion aperture defining an opening between said ionization source and said analytical gap,
      iv. a third electrode positioned proximate to said ion aperture,
      v. at least one outlet aperture from said analytical gap remote from said ion aperture,
      vi. an ion detector for measuring ions from said analytical gap and spaced from said electrodes, and
      vii. an electrical controller connected to said electrodes for impressing:
         A. direct current potentials to said first, second and third electrodes, and
         B. a periodic asymmetrical potential to said first and second electrode, said potentials capable of creating a transverse electric field therebetween during the flow of carrier gas in the analytical gap.

2. An ion mobility spectrometer as set forth in claim 1 wherein said first and second electrodes are cylindrical and coaxially aligned.

3. An ion mobility spectrometer as set forth in claim 1 wherein said first and second electrodes are planar.

4. An ion mobility spectrometer as set forth in claim 1 wherein said third electrode comprises the ionization source.

5. An ion mobility spectrometer as set forth in claim 1 wherein said electrical controller includes a third bias potential between the first and second electrodes, said third bias potential comprising a low frequency ripple voltage.

6. An ion mobility spectrometer as set forth in claim 1 wherein said ionization source is selected from the group consisting of a $\beta$-emitters, photoionizers, corona discharge ionizers, electrospray and thermal ionizer.

7. An ion mobility spectrometer as set forth in claim 2 wherein said ionization source includes an ion chamber coaxially aligned with said second electrode and spaced apart therefrom to define said ion aperture.

8. An ion mobility spectrometer as set forth in claim 1 wherein said housing includes a second inlet in communication with said analytical gap, said second inlet being connected to a source of carrier gas.

9. An ion mobility spectrometer as set forth in claim 1 wherein said housing includes a second inlet, said second inlet being connected to a sample media and said first inlet being connected to a source of carrier gas.

10. An ion mobility spectrometer as set forth in claim 1 wherein the said periodic asymmetric potential creates a field from 5 kv/cm to 30 kv/cm.

11. An ion mobility spectrometer as set forth in claim 1 wherein the value of asymmetry $\beta$ of said asymmetrical voltage is between about 0.1 and 0.7 for the waveform $v = v_o [(1-\beta) \cos \omega t + \beta \cos 2 \omega t]$.

12. An ion mobility spectrometer as set forth in claim 1 wherein said ionization source comprises a corona discharge, said corona discharge being coaxially aligned with said second electrode and including an electrical shield in any area coexistent with said second electrode.

13. An ion mobility spectrometer as set forth in claim 1 wherein said analyzer includes an ionization chamber in communication with sample media, said ionization source being positioned in this said chamber and said chamber being positioned adjacent said ion aperture.

14. An ion mobility spectrometer as set forth in claim 13 wherein said ionization chamber, ionization source, third electrode and first electrode are set at potentials with respect to each other to accelerate ions through said ion aperture.

15. An ion mobility spectrometer as set forth in claim 1 wherein said ionization source, third electrode, and first electrode are set at potentials with respect to each other to accelerate ions through said ion aperture.

16. An ion mobility spectrometer as set forth in claim 1 wherein said electric controller includes a bias voltage of low frequency impressed in series with said direct current compensating potential and periodic asymmetrical potential.

17. An ion mobility spectrometer as set forth in claim 12 wherein said electrical controller is adjustable to vary the potential difference between said ionization chamber and ionization source.

18. An ion mobility spectrometer as set forth in claim 1 in which said periodic asymmetrical potential has a waveform conforming to the general expression: $\int_o^T V^3 (t) \, dt \neq 0$.

* * * * *